United States Patent
Yang et al.

(10) Patent No.: US 10,206,905 B2
(45) Date of Patent: Feb. 19, 2019

(54) USE OF COMPOSITION FOR PREPARING A MEDICAMENT FOR TREATMENT OF AMYOTROPHIC LATERAL SCLEROSIS

(71) Applicant: JIANGSU SIMCERE PHARMACEUTICAL CO., LTD, Nanjing (CN)

(72) Inventors: Shibao Yang, Nanjing (CN); Yao Hua, Nanjing (CN); Zhengping Zhang, Nanjing (CN); Rong Chen, Nanjing (CN); Zhaolong Gong, Nanjing (CN)

(73) Assignee: JIANGSU SIMCERE PHARMACEUTICAL CO., LTD, Nanjing (CN)

( * ) Notice: Subject to any disclaimer, the term of this patent is extended or adjusted under 35 U.S.C. 154(b) by 0 days.

(21) Appl. No.: 15/574,693

(22) PCT Filed: Jun. 8, 2016

(86) PCT No.: PCT/CN2016/085269
§ 371 (c)(1),
(2) Date: Nov. 16, 2017

(87) PCT Pub. No.: WO2016/197945
PCT Pub. Date: Dec. 15, 2016

(65) Prior Publication Data
US 2018/0318261 A1    Nov. 8, 2018

(30) Foreign Application Priority Data
Jun. 10, 2015    (CN) .......................... 2015 1 0314584

(51) Int. Cl.
A61K 31/496    (2006.01)
A61K 31/4152    (2006.01)
(Continued)

(52) U.S. Cl.
CPC .......... *A61K 31/4152* (2013.01); *A61P 25/28* (2018.01); *A61K 31/045* (2013.01); *A61K 2300/00* (2013.01)

(58) Field of Classification Search
None
See application file for complete search history.

(56) References Cited

U.S. PATENT DOCUMENTS

| | | |
|---|---|---|
| 5,965,609 A | 10/1999 | Klar et al. |
| 2008/0161378 A1 | 7/2008 | Yoshino et al. |

(Continued)

FOREIGN PATENT DOCUMENTS

| | | | |
|---|---|---|---|
| CN | 101848711 B | | 4/2012 |
| CN | 103889415 | * | 9/2012 |

(Continued)

OTHER PUBLICATIONS

Database CAPLUS Chemical Abstracts Service, Columbus, Ohio, US; Database Accession No. 2016:2075773, Abstract of KR 2016141546, Moon et al., Dec. 9, 2016 (Year: 2016).*

(Continued)

*Primary Examiner* — Karl J Puttlitz
(74) *Attorney, Agent, or Firm* — Seed IP Law Group LLP (57) ABSTRACT

The present invention relates to the use of a composition for preparing a medicament for the treatment of amyotrophic lateral sclerosis and associated disorders. The composition comprises 3-methyl-1-phenyl-2-pyrazoline-5-one or pharmaceutically acceptable salts thereof and borneol. The medicament is a drug used for delaying the occurrence time of amyotrophic lateral sclerosis and extending the survival time, and for improving memory function defect of amyotrophic lateral sclerosis.

19 Claims, 3 Drawing Sheets
Specification includes a Sequence Listing.

(51) Int. Cl.
    *A61P 25/28*     (2006.01)
    *A61K 31/045*     (2006.01)

(56) References Cited

U.S. PATENT DOCUMENTS

2011/0003873 A1     1/2011    Yin et al.
2014/0228420 A1     8/2014    Yoneoka

FOREIGN PATENT DOCUMENTS

| CN | 10388915 A | 6/2014 |
|----|---|---|
| CN | 104546832 A | 4/2015 |
| JP | 11-503171 A | 3/1999 |
| JP | 2005-75434 A | 3/2005 |
| JP | 2011-513249 A | 4/2011 |
| JP | 2013-35712 A | 2/2013 |
| WO | 02/051395 * | 7/2002 |
| WO | 2005/075434 * | 8/2005 |
| WO | 2005/075434 A1 | 8/2005 |
| WO | 2013/035712 A1 | 3/2013 |

OTHER PUBLICATIONS

Notification of Reasons for Refusal, dated Aug. 14, 2018, for Japanese Application No. 2018-512476, 5 pages. (with English Translation).

* cited by examiner

USE OF COMPOSITION FOR PREPARING A MEDICAMENT FOR TREATMENT OF AMYOTROPHIC LATERAL SCLEROSIS

The Sequence Listing associated with this application is provided in text format in lieu of a paper copy, and is hereby incorporated by reference into the specification. The name of the text file containing the Sequence Listing is 500044.404USPC_SEQUENCE_LISTING.txt. The text file is 159 KB, was created on, Feb. 23, 2018, and is being submitted electronically via EFS-Web.

CROSS REFERENCE TO RELATED APPLICATIONS

This application claims priority to Chinese Patent Application No. 201510314584.4, filed to Patent Office of China on Jun. 10, 2015, entitled with "USE OF COMPOSITION FOR PREPARING A MEDICAMENT FOR TREATMENT OF AMYOTROPHIC LATERAL SCLEROSIS", which is hereby incorporated by reference in its entirety.

FIELD

The present invention relates to the field of pharmaceuticals, particularly relates to the use of the composition of 3-methyl-1-phenyl-2-pyrazolin-5-one or pharmaceutically acceptable salts thereof and borneol in treating amyotrophic lateral sclerosis and related disorders.

BACKGROUND

Motor neuron disease is a neurodegenerative disease of unknown etiology, primarily implicating cerebral cortex, brain stem and spinal motor neuron, including amyotrophic lateral sclerosis (ALS), progressive muscular atrophy, progressive bulbar paralysis and primary lateral sclerosis. Wherein, ALS is the most common type of motor neuron diseases. The onset age of ALS is between 50~60 years old, and the morbidity is 2/100000, which is characterized by the selective death of upper and lower motor neurons, resulting in progressive muscular atrophy, inertia and stiffness. The median survival time from the onset of ALS to death is 39 months, most patients generally die from respiratory failure in 3~5 years. About 5~10% of the familial ALSs are usually autosomal dominant;90~95% of the ALS cases are sporadic ALS (*Nat Rev Neurosci* 2001; 2: 806-819;*Annu Rev Neurosci* 2004; 27: 723-749).

About 20% of the familial ALSs are caused by the genetic mutation of the Cu/Zn superoxide dismutase (SOD1). Due to the similarities on the clinical manifestations of sporadic and familial ALSs, it is set forth that the potential mechanism of the familial ALS is useful for studying two forms of ALS. Hence, the transgenic mice carrying human mutant SOD1 opens the field of study on the familial ALS pathology (Neuron 2006; 52:39-59). It is indicated in recent research that there are abnormal SOD1 proteins in the spinal cord tissues from sporadic ALS and familial ALS patients, implying that SOD1 may play a role in both forms of ALS diseases (*Annu Rev Neurosci* 2004; 27: 723-749). In addition, it is found latest that there are RNA metabolism protein TDP-43genetic mutations in familial ALS autosome, meanwhile there are also pathological changes of TDP-43 proteins in most sporadic ALS patients, implying that TDP-43 may be of significant importance in understanding sporadic and familial ALSs (*Proc Natl Acad Sci USA* 2007;104: 12524-12529). The pathogenesis of ALS is complex, and the current biological hypothesis includes oxidative damage, accumulation of aggregates in cells, mitochondrial dysfunction, deficiency of axonal transport, lack of growth factor, colloid cell pathology and glutamate excitotoxicity (*Ann Neurol.* 2009 Jan; 65*Suppl* 1:S3-9).

3-methyl-1-phenyl-2-pyrazolin-5-one (edaravone), as a new potent free-radical scavenger, may scavenge hydroxyl radical (OH), nitric oxide radical (NO.), peroxynitrite ion (ONOO—) (*Chem Pharm Bull* 2004, 52(2):186-91; *Redox Rep.* 2002, 7(4): 219-22; *J Pharmacol Exp Ther.* 2007, 322 (1): 274-81), inhibit cell peroxidative damage; as an effective neuron protective agent (free-radical scavenger), may have advantages of wide distribution, short half-life, safe and low toxicity and is an effective first-line therapeutic drug in clinical ischemic stroke (Guidelines for the diagnosis and treatment of acute ischemic stroke in China, 2010). Edaravone has favorable neuroprotective effects in animal models with neurodegenerative diseases, such as animal models with β amyloid proteins (Aβ) injected in lateral ventricle and with streptozotocin (STZ) injected in lateral ventricle (*Biomed Res Int.* 2014;2014:370368; *Neurotoxicology.* 2013, 38:136-45). In addition, edaravone is capable of slowing the progression of the symptoms in mutant SOD1 G93A mice ALS and the degeneration of neuron (*Exp Neurol.* 2008, 213(2):448-55). Patent WO2005/075434 discloses the use of 3-methyl-1-phenyl-2-pyrazolin-5-one in treating amyotrophic lateral sclerosis. However, it is suggested in a clinical phase-III study that the score of the amyotrophic lateral sclerosis Functional Rating Scale-Revised (ALSFRS-R) in edaravone group decreased less than the placebo group, there was no significant difference; the study results of clinical trials have not reached the primary endpoint (NCT00330681; *Amyotroph Lateral Scler Frontotemporal Degener.* 2014 Dec;15(7-8):610-7). Another clinical phase-III experiment (NCT01492686) is ongoing, but has not been recruited.

Borneol is divided into synthetic borneol and natural borneol. Synthetic borneol contains isoborneol, while natural borneol contains no isoborneol. Natural borneol is also known as 2-camphol. It is suggested in a study that borneol is capable of improving intestinal absorption (AAPS Pharm Sci Tech. 2011 Dec;12(4):1044-9), blood-brain barrier (J Asian Nat Prod Res. 2014, 16(6): 648-57; J Ethnopharmacol. 2015, 162:270-7) and corneal permeability (Pharmazie.2006, 61(9):783-8), neuroprotective effect (Neuroscience. 2011, 176:408-19;Eur JPharmacol. 2014, 740:522-31), anti-inflammation (Inflammation. 2014, 37(4):1148-57), antioxidation and protecting DNA injuries (J Agric Food Chem. 2014, 62(28):6632-9), enhancing GABA receptor functions (*Biochem Pharmacol.* 2005, 69(7):1101-11), and also improving rat coagulation functions, antithrombotic activities (*Am J Chin Med.* 2008; 36(4):719-27).

The clinical III experimental study on the composition of 3-methyl-1-phenyl-2-pyrazolin-5-one and natural borneol with a mass ratio of 4:1 being useful for treating ischemic stroke has been developed in China. It was suggested in the preclinical animal experiments that the composition with a mass ratio of 4:1~1:1 can synergistically reduce the area of cerebral infarction (Patent CN 101848711 B), the composition with a mass ratio of 4:1~2:1 can synergistically reduce the mortality of animals with sepsis (Patent 201310474253.8).

Based on the prior art, it is unanticipated whether the composition of 3-methyl-1-phenyl-2-pyrazolin-5-one and borneol can be used in treating amyotrophic lateral sclerosis and related disorders, and it is not determinable whether the composition of 3-methyl-1-phenyl-2-pyrazolin-5-one and borneol with the current mass ratio of 4:1 has synergetic effects.

SUMMARY

It is an object of the invention to provide the use of a composition in preparing the medicaments for treating amyotrophic lateral sclerosis and related disorders, the composition contains 3-methyl-1-phenyl-2-pyrazolin-5-one or pharmaceutically acceptable salts thereof and borneol.

It is another object of the invention to provide a method for treating amyotrophic lateral sclerosis and related disorders, wherein the administration to patients in need thereof comprises the drug composition of 3-methyl-1-phenyl-2-pyrazolin-5-one or pharmaceutically acceptable salts thereof and borneol.

It is yet another object of the invention to provide a drug composition, the composition is used to treat amyotrophic lateral sclerosis and related disorders; wherein the composition comprises3-methyl-1-phenyl-2-pyrazolin-5-one or pharmaceutically acceptable salts thereof and borneol.

It is still another object of the invention to provide the use of 3-methyl-1-phenyl-2-pyrazolin-5-one or pharmaceutically acceptable salts thereof in preparing the medicaments for treating amyotrophic lateral sclerosis in conjunction with natural borneol.

Furthermore, the co-use of 3-methyl-1-phenyl-2-pyrazolin-5-one or pharmaceutically acceptable salts thereof and borneol in the drug composition may synergistically enhance the efficacy for treating amyotrophic lateral sclerosis.

In one embodiment of the invention, the drug composition may improve the onset time and survival time of ALS.

In another embodiment of the invention, the drug composition may improve the motor function of ALS.

In yet another embodiment of the invention, the drug composition may improve the memory impairment of ALS.

In the composition described in the invention, the weight ratio of 3-methyl-1-phenyl-2-pyrazolin-5-one or pharmaceutically acceptable salts thereof to borneol is 10:1~1:10, preferably is 4:1~1:1, further preferably is 4:1~2:1, more preferably is 4:1.

In the composition described in the invention, the molar ratio of 3-methyl-1-phenyl-2-pyrazolin-5-one or pharmaceutically acceptable salts thereof to borneol is 9:1~1:9, preferably is 4:1~1:1, further preferably is 3.5:1~2:1, more preferably is 3.5:1.

Borneol described in the invention preferably is natural borneol, the natural borneol is also known as 2-camphol.

The drug composition described in the invention may further include pharmaceutically acceptable excipients.

Excipients usually are pharmacologically nonactive substances formulated together with the active pharmaceutical ingredient ("API") used for drug treatment. When producing the dosage forms, excipients are often used to increase the amount of the preparation containing effective active ingredients (so often be known as "extenders", "fillers" or "diluents"), to allow for distributing the crude drugs conveniently and precisely. They also can serve for different purposes of enhancing the treatment, such as promoting the drug absorption or dissolution, or considering other pharmacodynamics.

More specifically, the composition of the invention can be formulated alone or in combination with pharmaceutically acceptable carriers or diluents into the drug composition, and can be formulated into preparations in forms of solid, semi-solid, liquid or gas, such as tablets, capsules, powders, granules, ointments, solutions, suppositories, injections, inhalants, gels, microspheres and aerosols. Therefore, the administration of the compounds can be achieved by various routes, including orally, buccally, rectally, parenterally, intraperitoneally, intradermally, transdermally, intratracheally, intraarticularly, etc. The active agents may be systematic after the administration, or may be located by using regional administration, intra-wall administration or by using the implants which are capable of holding the active dosage in the implanting sites. In specific embodiments, the preparations are oral preparations.

The combination therapies used in the invention may allow the dosage of each monotherapy below that currently used in the standard operation, meanwhile achieve significant effects, including the effects beyond that achieved by conventionally giving any one of monotherapies. Those skilled in the art will readily recognize that the dosage level may change depending on the specific compound, the severity of symptom and the sensitivity of the subject to side effects. Some specific compounds are more effective than others. The preferred dosage of the designated compound may be easily ascertained in many ways by those skilled in the art. The preferred means is to measure the physiological effect of the designated compound. The use of combination therapies may allow the dosage of each monotherapy below that currently used in the standard operation, meanwhile achieve significant effects, including the effects greater than that achieved by conventionally giving any one of monotherapies.

DETAILED DESCRIPTION

The following embodiments only illustrated the present invention by way of examples, and should not be considered as limiting the present invention. Edaravone mentioned in the embodiments is 3-methyl-1-phenyl-2-pyrazolin-5-one, borneol is natural borneol, i.e. 2-camphol, and the composition is the composition of 3-methyl-1-phenyl-2-pyrazolin-5-one and natural borneol.

EXAMPLE 1

Study on the Therapeutic Effects of the Composition of Edaravone and Borneol on the Transgenic Mice with Amyotrophic Lateral Sclerosis 1 Materials and Methods
1.1 Testing Animals The transgenic mice (B6SJL-TgN[SOD1-G93A] 1Gur) carrying humanized copper/zinc superoxide dismutase (SOD1) (G93A mutants) and wild-type B6SJL F1 mice are purchased from Nanjing University. The breed conversation and propagation methods of the mice: one wild-type female mouse and one transgenic male mouse are allowed to mate with each other, with their progeny identified through polymerase chain reaction (PCR) with DNA extracted from the tail of young mice.

1.2 Drugs and Reagents

The composition of edaravone and borneol, with a mass ratio of 4:1 (said borneol is 2-camphol);
edaravone (chemical name: 3-methyl-1-phenyl-2-pyrazolin-5-one);
borneol (chemical name: 2-camphol)
1.3 Test Methods
1.3.1 Breeding and screening of B6SJL-TgN(SOD1-G93A)1Gur mice:

5 B6SJL-TgN(SOD1-G93A)1Gur male mice were allowed to mate with B6SJLF1 female healthy mice in a ratio of 1 male to 3 females beginning at the age of 60 d. DNA was extracted from the progeny mice tail-cutting (as required in the kits), plus SOD1 primers 5' -CATCAGC-CCTAATCCATCTGA-3 ' and 5 ' -CGCGACTAACAATCA AAGTGA-3 ' were amplified through 30 PCR cycles, confirming SOD1 gene strips between 200~300bp. Mice without SOD1 mutant gene were eliminated.

1.3.2 Behavior Examination:

According to the methods reported in literatures, mice were placed on the Rota-rod (60 Hz/min, Φ190 mm), and the time from being placed on the Rota-rod to dropping was recorded. Each mouse was determined for 3 times at each time point, with the longest time of mouse keeping on the rotating rod reflecting the motor function of the mouse, the determination was stopped if the time was over 180s, calculated as 180s. The motor functions of the mice with SOD1 mutant gene were determined beginning at the age of 60 d. Thereafter, they were observed and determined every 10 days, until death.

1.3.3 Treating Process
1.3.3.1 Experimental Dosage Settings and Grouping:

Calculated based on the effective doses of edaravone (SOD1-G93Amouse15 mg/kg, SOD1-H46R rat 3-6mg/kg) and those on cerebral ischemic animal models (SD rat 6 mg/kg) according to the literature, the dosage of edaravone was set at 12 mg/kg, then the dosage of the composition of edaravone and borneol was set at 15 mg/kg (the dosage of edaravone was set at 12 mg/kg, borneol was 3 mg/kg), and borneol was set at 3 mg/kg.

SOD1 genetic mutant mice at the age of 70 d were divided randomly into 4 groups according to their motor functions. Respectively: the SOD1 genetic mutation control group; the treating group of the composition of edaravone and borneol at 15 mg/kg; the treating group of edaravone at 12 mg/kg; the treating group of borneol at 3 mg/kg; another B6SJL healthy mice control group without SOD lgenetic mutation was additionally set. There was 14 mice each group, half of males and half of females.

1.3.3.2 Experimental Dosing:

From the day of grouping, animals in each group were dosed by intraperitoneal injection once a day, until death. Animals in the healthy control group and the SOD1 genetic mutation control group were given saline of equal volumes.

1.3.4 Onset Time and Survival Time:

It was determined as muscle strength decline when the time of the mice keeping on the rotarod decreased by over 30% compared with the former time determined. The onset time of the mice was determined according to the variation of this motor function and the observation of the anterior limbs of the mice with or without tremor. When the mice have lain on their backs on smooth planes for 30 s and cannot righting reflex, or there was serious infection in one or both eyes, then the mice may be judged as death and sacrificed. The time from birth to death of a mouse was the survival time of the mouse.

1.4 Statistical Treatment: Variance Analysis was Performed using the SPSS Statistical Software (Multi-group Comparison).

2 Test Results 2.1 Effects on the Survival Time of SOD1-G93A Mice

Mice in SOD1-G93A control group came on around the age of 113 d, and the average survival time was (138.4±4.6) d. The composition group and the edaravone group were dosed beginning at 70 d of the mice, with no influence on the onset time of the mice, but being capable of extending the survival time of the mice significantly, and the average survival time of the composition group was (151.1±7.0)d, and that of edaravone was (144.6±3.7)d; the effects of borneol on the survival time had no statistical difference compared with the model group, being (141.3±3.6)d. The survival time of the composition was longer markedly than that of edaravone and borneol single-drug, indicating that the efficacy of the composition was superior to those of two single-drugs, see Table 1. There was no clinical symptom with B6SJL healthy mice, with the survival time over 1 year.

It was assessed whether there was a synergistic effect between edaravone and borneol in the composition according to the Jong-eun's formula, $q=E(a+b)/(Ea+Eb-Ea \times Eb)$. In the formula, E(a+b) is the effective rate of the combined drugs, Ea, Eb is the effective rate of A drug, B drug used alone, respectively. If q value was in the range of 0.85~1.15, indicating the sum of the combined two drugs; q value >1.15 indicating enhancement, and q value <0.85 indicating there was an antagonistic effect when two drugs were used together. Calculated based on the above formula, q=1.37, indicating there was a synergistic effect among the components of the composition, with the combined drugs superior to the single-drug.

TABLE 1

Effects of the composition, edaravone and borneol on the onset time and survival time of SOD1-G93A mice

| Group | Dosage (mg/kg/d) | Number of animals | | Onset Time (d) | Survival Time (d) | Survival Time Extension (d) |
|---|---|---|---|---|---|---|
| | | Male | Female | | | |
| SOD1-G93A control | — | 7 | 7 | 113.8 ± 2.9 | 138.4 ± 4.6 | — |
| Composition of edaravone and borneol | 15 | 7 | 7 | 112.8 ± 3.5 | 151.1 ± 7.0* | 12.7 |
| Edaravone | 12 | 7 | 7 | 113.7 ± 2.6 | 144.6 ± 3.7*# | 6.2 |
| Borneol | 3 | 7 | 7 | 113.1 ± 2.5 | 141.3 ± 3.6# | 2.9 |

Figure 1:
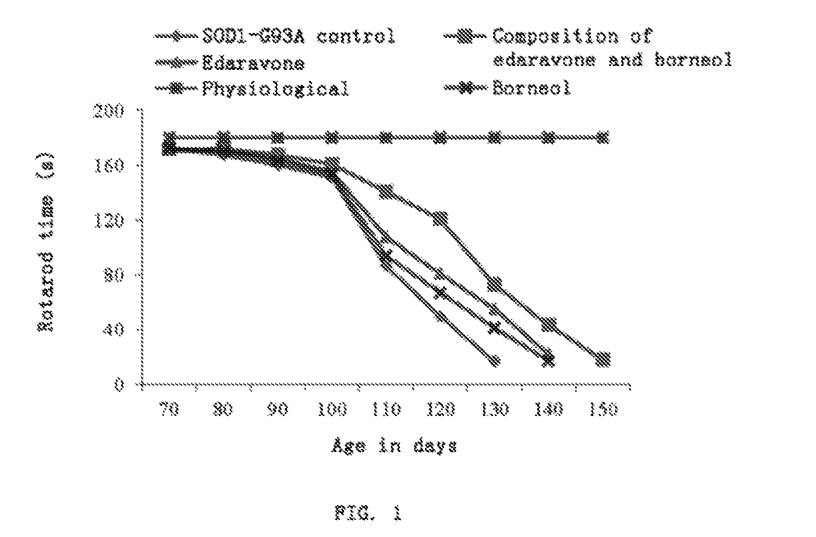
FIG. 1 Effects of each group in Embodiment 1 on the motor function of SOD1-G93A mice.

Note:
*$p < 0.05$, compared with the SOD1-G93A control group;
$p < 0.05$, compared with the group of the composition of edaravone and borneol 2.2 Effects on the Motor Function of SOD1-G93A Mouse As can be seen from FIG. 1, both the composition and edaravone may significantly slow the decline of the muscle strength of SOD1-G93A mouse, improve the animal motor function, the effects of the rotarod time at the age of 110, 120, 130 d have statistical difference compared with the model control group ($p<0.05$); borneol also had some tendency to slow the progress of disease, but only the effects on the rotarod time at the age of 130 d was different significantly from the model group ($p<0.05$). Also, the effects of the composition at the age of 110, 120, 130 d are markedly superior to those of edaravone and borneol ($p<0.05$).

EXAMPLE 2

Effect of the Composition of Edaravone and Borneolon the Learning Memories of the Transgenicmice with Amyotrophic Lateral Sclerosis 1 Materials and Methods
1.1 Testing animals The transgenic mice (B6SJL-TgN[SOD1-G93A] 1Gur) carrying humanized copper/zinc superoxide dismutase (SOD1) (G93A mutants)and wild-type B6SJL F1 mice are purchased from Nanjing University. The breed conversation and propagation methods of the mice: one wild-type female mouse and one transgenic male mouse were allowed to mate with each other, with their progeny identified through polymerase chain reaction (PCR) with DNA extracted from the tail of young mice.

1.2 Drugs and Reagents

The composition of edaravone and borneol (said borneol is 2-camphol);

edaravone (chemical name: 3-methyl-1-phenyl-2-pyrazolin-5-one);

borneol (chemical name: 2-camphol).

1.3 Test Methods 1.3.1 Breeding and Screening of B6SJL-TgN(SOD1-G93A)1Gur Mice:

5 B6SJL-TgN(SOD1-G93A)1Gur male mice were allowed to mate with B6SJLF1 female healthy mice in a ratio of 1 male to 3 females beginning at the age of 60 d. DNA was extracted from the progeny mice tail-cutting (as required in the kits), plus SOD1 primer5'-CATCAGC-CCTAATCCATCTGA-3' and 5'-CGCGACTAACAAT-CAAA GTGA-3' were amplified through 30 PCR cycles, confirming SOD1 gene strips between 200~300bp. Mice without SOD1 mutant gene were eliminated.

1.3.2 Experiment Process
1.3.2.1 Experimental Dosage Settings and Grouping:

Calculated based on the effective doses of edaravone (SOD1-G93Amouse 15 mg/kg, SOD1-H46R rat 3-6 mg/kg) and those on cerebral ischemic animal models (SD rat 6 mg/kg) according to the literature, the dosage of edaravone was set at 12 mg/kg, then the dosage of the composition of edaravone and borneol was set at 15 mg/kg (the dosage of edaravone was set at 12 mg/kg, borneol was 3 mg/kg), and borneol was set at 3 mg/kg.

SOD1 genetic mutant mice at the age of 70 d were divided randomly into 4 groups according to their motor functions. Respectively: the SOD1 genetic mutation control group; the treating group of the composition of edaravone and borneol at 15 mg/kg; the treating group of edaravone at 12 mg/kg; the treating group of borneol at 3 mg/kg; another B6SJL healthy mice control group without SOD1 genetic mutation was additionally set. There was 14 mice each group, half of males and half of females.

1.3.2.2 Experimental Dosing:

From the day of grouping, animals in each group were dosed by intraperitoneal injection once a day, until the behavior test has been completed. Animals in the healthy control group and the SOD1 genetic mutation control group were given saline of equal volumes.

1.3.2.3 Behavior Test

The passive avoidance test was performed when the animals were at the age of about 90 d to determine their abilities of learning and memory. The experimental device was divided into two rooms, bright and dark. The bright room was illuminated with a 5 w LED lamp, and there was a little gate between two rooms. The experiment was performed in three days. Animals were accommodated on the first day. The mice were placed in the bright room with face back to the hole, and were allowed to move freely between the bright room and the dark room, without current stimulation in both rooms for the duration of 5 min. The learning experiment was carried out on the next day. The mice were placed into the bright room with face back to the hole in the test, the timer was initiated at the same time, and the animals entered the dark room through passing the hole, subjecting to the electric shock (0.19 mA), the recorded time was the latency period, meanwhile recording the number of step-through errors in 5 min after the mice got into the dark room. The memory experiment was carried out on the third day, the time from placing each mouse into the bright room to entering the dark room was recorded, if the mouse didn't enter the dark room in 5 min, then the latency period was recorded as 300s, meanwhile recording the number of step-through errors in 5 min after the mice got into the dark room.

1.4 Statistical treatment: Variance Analysis was Performed by Employing the SPSS Statistical Software (Multi-group Comparison).

Figure 2:
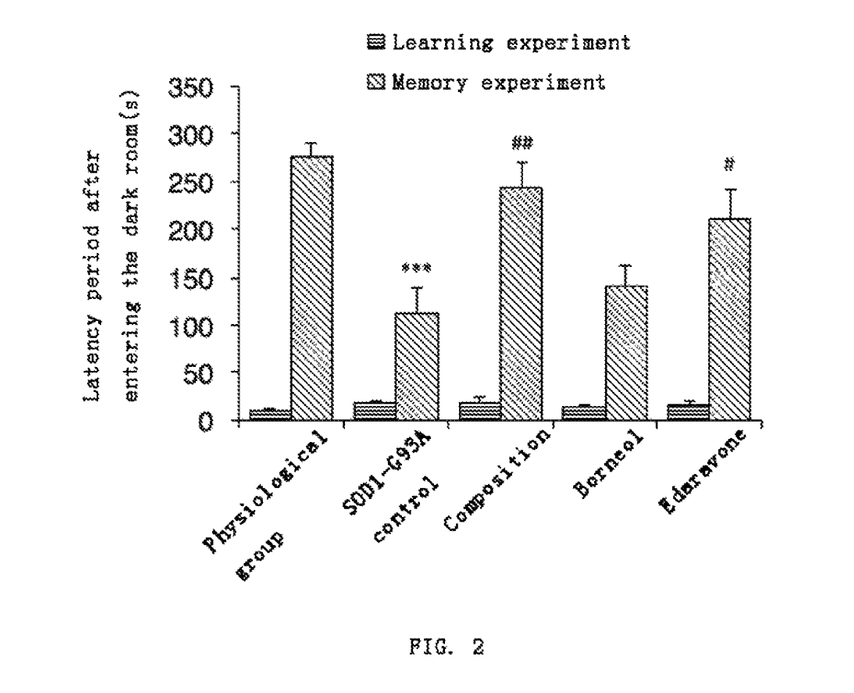
FIG. 2 Effects of each group in Embodiment 2 on the latency period of SOD1-G93A mice after entering the dark room.

2 Test Results 2.1 Effects on the Latency Period after Entering the Dark Room in the Passive Avoidance Test Effects on the latency period after entering the darkroom in the passive avoidance test can be seen in FIG. 2 (The histogram data was expressed as mean ±standard error. ***$P < 0.001$, compared with the physiological control group; #$P < 0.05$, ##$P < 0.01$, compared with the model group). In the learning experiment, there was no statistical significance among groups through the one-way analysis of variance. In the memory experiment, the latency period after entering the dark room in SOD1-G93A model group was shorten significantly compared with that in the physiologic control group ($p < 0.05$). The latency period after entering the dark room in the composition and edaravone group was extended significantly compared with that in the model group ($p < 0.05$), the effect of borneol was not obvious. It was suggested from the experiment results that the abilities of learning and memory of SOD1-G93A animals declined significantly in the progress of the disease, the composition of edaravone and borneol and edaravone were capable of improving the memory impairment obviously, and the efficacy of the composition was better than that of single-drug.

It was assessed whether there was a synergistic effect between edaravone and borneol in the composition according to the Jong-eun's formula, $q = E(a+b)/(Ea + Eb - Ea \times Eb)$. In the formula, Ea+b is the effective rate of the combined drugs, Ea, Eb is the effective rate of A drug, B drug used alone, respectively. If q value was in the range of 0.85~1.15, indicating the sum of the combined two drugs; q value >1.15 indicating enhancement, and q value <0.85 indicating there was an antagonistic effect when two drugs were used together. Calculated based on the above formula, $q = 1.29$, indicating there was a synergistic effect among the components of the composition, with the combined drugs superior to the single-drug.

2.2 Effects on the Number of Step-through Errors in the Passive Avoidance Test

Figure 3:
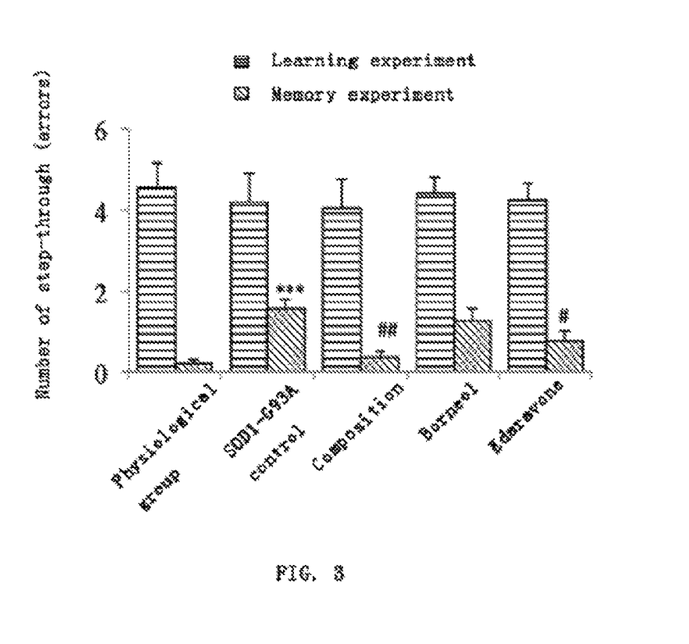
FIG. 3 Effects of each group in Embodiment 2 on the number of step-through errors of SOD1-G93Amice.

Effects on the number of step-through errors in the passive avoidance test can be seen in FIG. 3 (The histogram data was expressed as mean ±standard error. ***$P < 0.001$, compared with the physiological control group; #$P < 0.05$, ##$P < 0.01$, compared with the model group). In the learning experiment, there was no statistical significance among groups through the one-way analysis of variance. In the memory experiment, the number of step-through errors in the model group increased significantly compared with that in the physiologic control group ($p < 0.05$).The number of step-through errors in the composition and edaravone group decreased significantly compared with that in the model group ($p < 0.05$), the effect of borneol was not obvious. It was suggested from the experiment results that the abilities of learning and memory of SOD1-G93A animals declined significantly in the progress of the disease, the composition of edaravone and borneol and edaravone were capable of improving the memory impairment obviously, and the efficacy of the composition was better than that of single-drug.

Calculated based on the above Jong-eun's formula, $q = 1.25$, indicating there was a synergistic effect among the components of the composition, with the combined drugs superior to the single-drug.

EXAMPLE 3

Study on the Treating Effect of the Composition of Edaravone and Borneol on the Transgenic Mice with Amyotrophic Lateral Sclerosis 1 Materials and Methods 1.1 Testing Animals The transgenic mice with amyotrophic lateral sclerosis (B 6 SJL-Tg(SOD1*G93A)1Gur/JNj u, hereinafter referred to as SOD1-G93 A mice) and the wild-type control mice were purchased from Nanjing Biomedical Research Institute of Nanjing University.

1.2 Drugs and Reagents

Composition of Edaravone and natural borneol (the mass ratio of edaravone to natural borneol is 4:1)

Edaravone

Riluzole 1.3 Testing Program 1.3.1 Experimental Grouping

Experimental animals were divided into 6 groups, the wild control (Wt) group, the model (Tg) group, the positive drug Riluzole (Tg-Riluzole) group, the positive drugedaravone15mg/kg (Tg-E15) group, the composition 5 mg/kg (Tg-05 group, 15 mg/kg (Tg-C15) group, respectively. The mass ratio of edaravone to natural borneol in the composition group was 4:1.

1.3.2 Experimental Dosing

Dosing to animals was initiated from the age of 10 weeks, keeping on the whole survival period. Each dosage of the composition and the positive drug edaravone group was dosed by intraperitoneal injection once a day. The drug in the positive drug Riluzole group was dissolved in drinking water, 100 µg/ml. Animals in the wild control group and the model group were given the corresponding volumes of solvents by intraperitoneal injection.

1.3.3 Experimental Process

From the age of 10 weeks, the body weight, the motor function (motor ability score, rotarod test) of animals had been monitored once a week. Two consecutive rod droppings in the animal rotarod test had been considered as the sign of the onset of animal diseases. It was defined as the end of a disease to euthanasia when the animal cannot get righting in 30 seconds after being laid on one side.

1.3.4 Detection Index

The body weight, the motor ability score, the variation of the rod drop latency period with the time in the rotarod test, the onset time, and the survival time were considered as the indexes of observing the disease progress.

1.3.5 Test Methods 1.3.5.1 Motor Function Scores

Posterior limb: 3, no weak;2, one limb paralysis (one limb tremor when tail-lifting);1, lower limb paresis (both weak legs, but be capable of moving);0, paraplegia (legs cannot move)

Anterior limb: 3, no weak; 2, paresis (being capable of gripping the pull rod gently);1, paralysis (cannot grip the pull rod, but be capable of holding up the chest to leave the ground);0, cannot hold up the chest to leave the ground Trunk: 1, capable of turning around the trunk when dropped from the rotarod; 0, cannot do the above action Whole body activity: 3, capable of running; 2, capable of walking or creeping;1, capable of righting; 0, incapable of righting in 30 seconds The sum of scores in each part was the aggregate of the motor function scores.

1.3.5.2 Rotarod Test

Consecutive training was performed for three days in the 10th week. Detection was initiated from the 11th week, and the rotational speed of the rotarod was 14 rpm. The rod-drop latency periods of the animals were recorded, the longest duration was 180s. Recordings were carried out for three times, with the longest duration recorded.

1 Test Results 2.1 Effects on the Survival Time of SOD1-G93A Mice

Mice in SOD1-G93A control group came on around the age of 110 d, and the average survival time was (141.4.±11.1) d. Each dosing group was dosed beginning at 70 d of the mice, with no influence on the onset time of the mice, but being capable of extending the survival time of the mice significantly, see Table 2. The prolonged effect of the composition on the survival time had a certain dose-effect relationship, with the effect of high-dose superior to those of the positive drug, daravone and Riluzole. There was no clinical symptom with the wild control mice.

Figure 5:
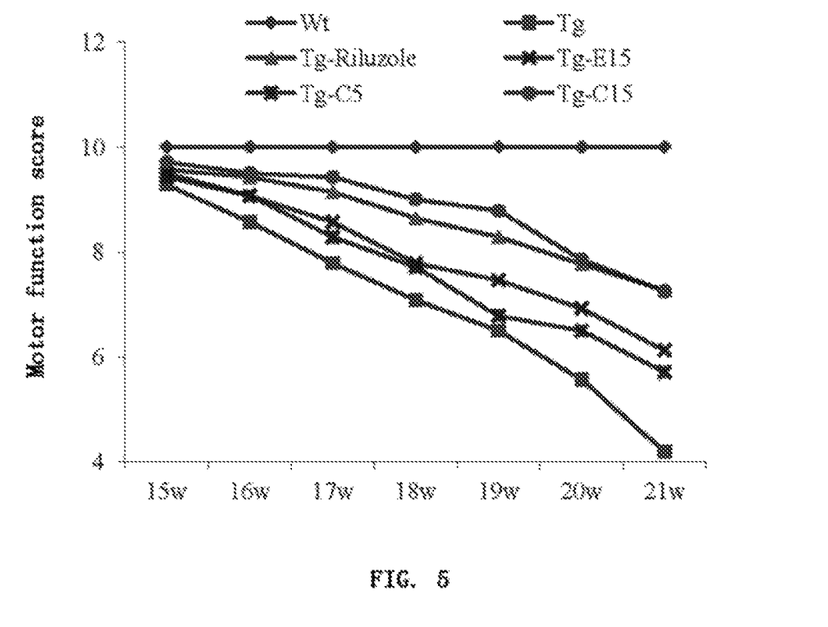
FIG. 5 Effects of each group pair in Embodiment 3 on the motor function scores of SOD1-G93A mice.

2.3 Effects on the Motor Function of SOD1-G93A Mice 2.3.1 Effects on the Motor Function Scores of SOD1-G93A Mice As can be seen in FIG. 5, the motor function scores of the mice in SOD1-G93Acontrol group decreased gradually from the 16th week. Compared with the model group, each dosing group may delay the decline progress of the motor function of SOD1-G93A mice to different degrees. The scores of the mice at the age of 16-21 weeks in Riluzole and the composition high-dose groups were significantly higher than in the model group (p<0.05), the scores of animals at the age of 17, 20, 21 weeks in daravone group were significantly higher than in the model group (p<0.05), the scores of animals at the age of 21 weeks in the composition low-dose group were significantly higher than in the model group (p<0.05). The efficacy of the composition has a certain dose-effect relationship, with the high-dose effect superior to the positive drugs, edaravone and Riluzole.

2.3.2 Effects on the Drop Time in the Rotarod Test of SOD1-G93A Mice

Figure 6:
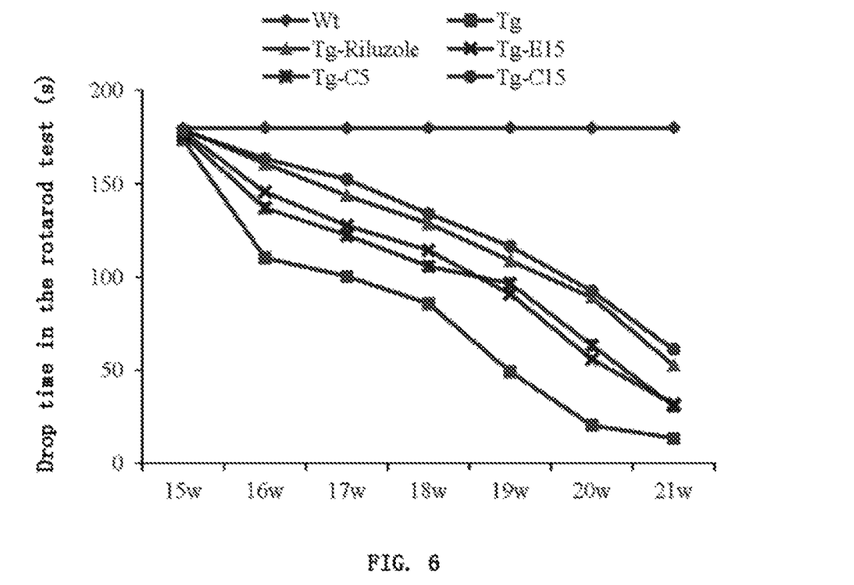
FIG. 6 Effects of each group in Embodiment 3on the drop time in the rotarod test of SOD1-G93A mice.

As can be seen in FIG. 6, the drop time in the rotarod test of the mice in SOD1-G93Acontrol group decreased gradually from the 16th week. Compared with the model group, each dosing group may significantly delay the drop time of SOD1-G93A mice, improve the motor function of animals.

TABLE 2

Effects of the composition on the onset time and survival time of SOD1-G93A mice (mean ± standard error)

| Group | Dosage (mg/kg/d) | Number of animals Male | Number of animals Female | Onset Time (d) | Survival Time (d) | Survival Time Extension (d) |
|---|---|---|---|---|---|---|
| Wild control | — | 7 | 7 | — | — | — |
| SOD1-G93A control | — | 7 | 7 | 110.0 ± 10.8 | 141.4. ± 11.1 | — |
| Riluzole | 100 μg/ml, in drinking water | 7 | 7 | 109.2 ± 9.4 | 155.8 ± 8.3*** | 15.6 |
| Edaravone | 15 | 7 | 7 | 111.3 ± 10.0 | 151.7 ± 9.7* | 9.4 |
| Composition, low-dose | 5 | 7 | 7 | 110.5 ± 17.3 | 149.3 ± 8.5* | 7.8 |
| Composition, high-dose | 15 | 7 | 7 | 109.5 ± 15.0 | 156.6 ± 11.3** | 16.1 |

Figure 4:
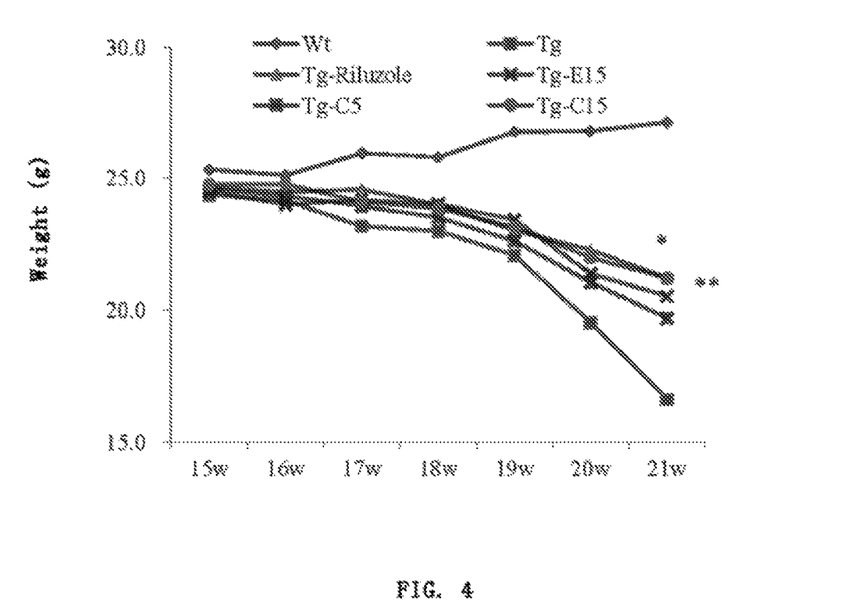
FIG. 4 Effects of each group pair in Embodiment 3 on the weights of SOD1-G93A mice.

Note:
*p < 0.05,
**p < 0.01,
***p < 0.001, compared with SOD1-G93A control group 2.2 Effects on the Weight of SOD1-G93A Mice As can be seen in FIG. 4, the weights of the mice in SOD1-G93Acontrol group have declined gradually from the 16th week. Compared with the model group, each dosing group may delay the decline progress of the weight of SOD1-G93A mice to different degrees, wherein the weights of animals at the age of 21 weeks in Riluzole (Tg-Riluzole) group and the composition high-dose (Tg-C15) group were significantly higher than in the model control group (p<0.05).

The drop time of mice at the age of 16-21 weeks in Riluzole and the composition high-dose groups was longer than in the model group markedly(p<0.05), the drop time of animals at the ages of 16, 19, 20, 21 weeks in edaravone group was markedly longer than in the model group (p<0.05), the drop time of animals at the ages of 19, 20, 21 weeks in the composition low-dose group was markedly longer than in the model group (p<0.05). The efficacy of the composition has a certain dose-effect relationship, with the high-dose effect superior to the positive drugs, edaravone and Riluzole.

The invention claimed is:

1. A method for treating amyotrophic lateral sclerosis, comprising: administering to a subject in need thereof an effective amount of a composition comprising 3-methyl-1-phenyl-2-pyrazolin-5-one or pharmaceutically acceptable salts thereof and borneol.

2. The method of claim 1, wherein the weight ratio of 3-methyl-1-phenyl-2-pyrazolin-5-one or pharmaceutically acceptable salts thereof to borneol is 10:1~1:10.

3. The method of claim 1, wherein the weight ratio of 3-methyl-1-phenyl-2-pyrazolin-5-one or pharmaceutically acceptable salts thereof to borneol is 4:1~1:1.

4. The method of claim 1, wherein the weight ratio of 3-methyl-1-phenyl-2-pyrazolin-5-one or pharmaceutically acceptable salts thereof to borneol is 4:1.

5. The method of claim 1, wherein the method is for improving the survival time of amyotrophic lateral sclerosis.

6. The method of claim 1, wherein the method is for improving the memory impairment of amyotrophic lateral sclerosis.

7. The method of claim 1, wherein the molar ratio of 3-methyl-1-phenyl-2-pyrazolin-5-one or pharmaceutically acceptable salts thereof to borneol is 3.5:1~2:1.

8. The method of claim 1, wherein the borneol is natural borneol.

9. The method of claim 1, wherein the composition further comprises pharmaceutically acceptable excipients.

10. The method of claim 1, wherein the molar ratio of 3-methyl-1-phenyl-2-pyrazolin-5-one or pharmaceutically acceptable salts thereof to borneol is 3.5:1.

11. The method of claim 2, wherein the method is for improving the survival time of amyotrophic lateral sclerosis.

12. The method of claim 2, wherein the method is for improving the memory impairment of amyotrophic lateral sclerosis.

13. The method of claim 2, wherein the borneol is natural borneol.

14. The method of claim 3, wherein the method is for improving the survival time of amyotrophic lateral sclerosis.

15. The method of claim 3, wherein the method is for improving the memory impairment of amyotrophic lateral sclerosis.

16. The method of claim 3, wherein the borneol is natural borneol.

17. The method of claim 4, wherein the method is for improving the survival time of amyotrophic lateral sclerosis.

18. The method of claim 4, wherein the method is for improving the memory impairment of amyotrophic lateral sclerosis.

19. The method of claim 4, wherein the borneol is natural borneol.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: PCR forward primer for mouse SOD1 gene

<400> SEQUENCE: 1
catcagccct aatccatctg a                                              21

<210> SEQ ID NO 2
<211> LENGTH: 21
<212> TYPE: DNA
<213> ORGANISM: Artificial
<220> FEATURE:
<223> OTHER INFORMATION: PCR reverse primer for mouse SOD1 gene

<400> SEQUENCE: 2
cgcgactaac aatcaaagtg a                                              21
```